(12) United States Patent
Mody

(10) Patent No.: US 6,454,740 B1
(45) Date of Patent: Sep. 24, 2002

(54) DOUBLE-LOOP CATHETER

(75) Inventor: Malay K. Mody, Copley, OH (US)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 09/478,182

(22) Filed: Jan. 5, 2000

(51) Int. Cl.⁷ .............................................. A61M 37/00
(52) U.S. Cl. .................................. 604/95.04; 604/528
(58) Field of Search .......................... 604/95.04, 95.01, 604/95.02, 95.03, 95.05, 528, 525, 532, 534, 530, 523, 241, 164.04, 103.04

(56) References Cited

U.S. PATENT DOCUMENTS

| | | | |
|---|---|---|---|
| 3,119,392 A | | 1/1964 | Zeiss et al. .................. 128/328 |
| 4,586,923 A | | 5/1986 | Gould et al. .................. 604/95 |
| 4,740,195 A | | 4/1988 | Lanciano ...................... 604/95 |
| 5,041,085 A | | 8/1991 | Osborne et al. .............. 604/51 |
| 5,213,575 A | * | 5/1993 | Scotti ....................... 604/95.04 |
| 5,352,198 A | * | 10/1994 | Goldenberg et al. ..... 604/95.04 |
| 5,399,165 A | * | 3/1995 | Paul, Jr. ...................... 604/95 |
| 5,419,764 A | | 5/1995 | Roll ............................. 604/95 |
| 5,727,555 A | * | 3/1998 | Chait ......................... 128/658 |
| 5,928,208 A | | 7/1999 | Chu et al. ................... 604/280 |
| 5,941,849 A | * | 8/1999 | Amos, Jr. et al. ............ 604/95 |

FOREIGN PATENT DOCUMENTS

| | | |
|---|---|---|
| EP | 0 320 144 A1 | 6/1989 |
| EP | 0 352 955 A2 | 1/1990 |
| EP | 0 417 865 A1 | 3/1991 |
| EP | 0 471 429 A2 | 2/1992 |
| EP | 0 531 040 A1 | 3/1993 |
| EP | 0 609 020 A1 | 8/1994 |
| EP | 0 700 692 A1 | 3/1996 |
| EP | 0 795 339 A1 | 9/1997 |
| JP | 6-190051 | 7/1994 |
| JP | 10-211286 | 8/1998 |
| SU | 1049066 A | 10/1983 |
| WO | WO 99/16355 | 4/1999 |

\* cited by examiner

*Primary Examiner*—Anhtuan T. Nguyen
*Assistant Examiner*—Matthew DeSanto
(74) *Attorney, Agent, or Firm*—Richard J. Godlewski

(57) ABSTRACT

A catheter(10) includes an elongated tubular member (14) having a proximal end (34) opposite a distal end (36). The distal end has a loop hole (70), at least one transition hole (72), and an end hole (78). A thread (60) has one end (62) fixed at the proximal end. The thread extends through the interior of the tubular member and out from the loop hole. The thread then extends through the transition hole and re-enters the tubular member at the end hole (78). The thread has a pulling end (64) exiting the tubular member at the proximal end. Application of a pulling force on the pulling end causes the distal end to form a first loop from the loop hole to the transition hole and a second loop from the transition hole to the end hole. The tubular member has a plurality of drainage/infusion ports (40) between the distal end and the end hole. The ports are in a radial position substantially opposite the radial position of the loop hole. The catheter (10) further includes a hub (12) having a channel (20) therethrough. The hub is coupled to the tubular member and a pivotable locking member (24) is coupled to the hub. The locking member secures the thread to the hub after the thread is fully pulled. The number of loops formed can be increased by adding more transition holes.

15 Claims, 3 Drawing Sheets

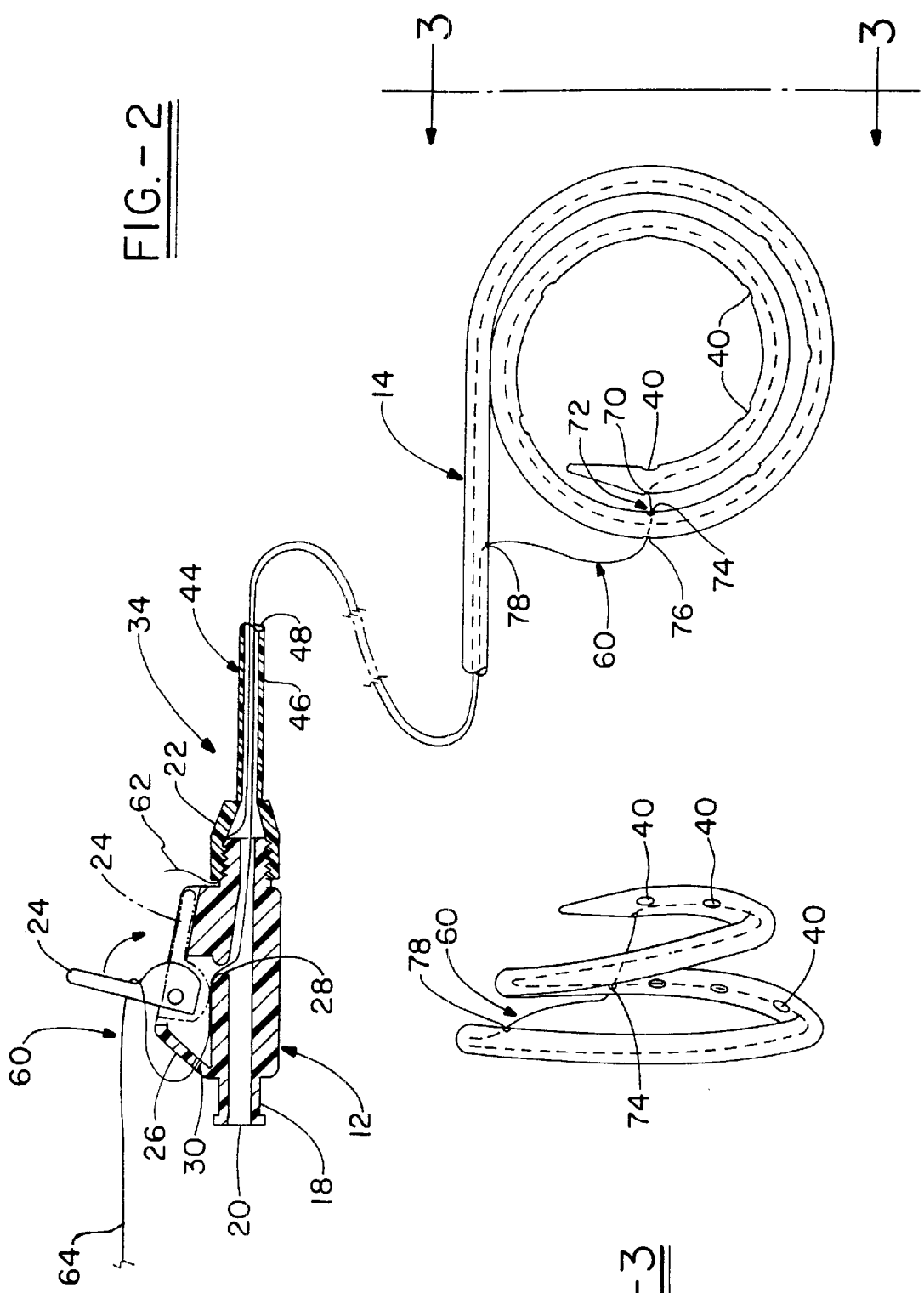

DOUBLE-LOOP CATHETER

TECHNICAL FIELD

This invention relates to catheters for draining fluid from a body cavity or for infusing medication into a body cavity. Particularly, this invention relates to a drainage/infusion catheter which forms multiple loops within the cavity to preclude inadvertent withdrawal of the catheter.

BACKGROUND ART

The use of catheters for draining excess or infected body fluids from a body cavity or for infusing medication into a body cavity is well known. One use of the catheter is to drain excess fluid. For example, the catheter can be used to drain urine from the kidney when there is an obstruction in the ureter. Another use of the catheter is to drain fluid from an infected collection. For example, the catheter can be used to drain pus from an abdominal abscess. Inserting a drainage catheter into a body cavity is done with the aid of an insertion tool, such as a stiffening cannula. Once in position, the flexible distal portion at the end of the catheter is altered to essentially maintain the flexible distal portion within the cavity and, in turn, to preclude inadvertent removal of the catheter from the body cavity. Excess or infected fluid enters a port or hole in the tubular member of the catheter and is withdrawn from the cavity by aspiration or gravity.

To prevent the catheters from being inadvertently removed during use, it is known to provide a mechanism for imparting a single loop at the distal flexible end of the catheter. This loop is much larger than the hole through which the catheter is inserted and is thereby retained in the cavity. Although forming of a single loop at the end of the catheter has been shown effective in use, it is still subject to dislodging by movement of the patient, as the patient gets in and out of bed or as the patient rolls over while sleeping. The catheter can also get pulled out during dressing changes by a nurse or when the patient is getting ready and it gets caught on something and pulled out. Of course, dislodging of the catheter is an unacceptable situation. First, the catheter is not functioning properly and can affect the well-being of the patient. Such a situation may lead to a persistence of excess fluid or an infection within the patient. And the patient must undergo another catheterization.

Thus, the need exists for a catheter which allows for imparting additional loops within the body cavity to further enhance its ability to stay within the cavity as the patient receives care and moves about.

DISCLOSURE OF INVENTION

It is thus an object of the present invention to provide a double- or multiple-loop catheter.

It is another object of the present invention to provide a catheter, as above, which includes a hub with an elongated hollow tubular member extending therefrom, wherein the tubular member is inserted into the cavity to be drained or into which medication is to be deposited.

It is a further object of the present invention to provide a catheter, as above, which includes a thread that extends through the hollow tubular member for coiling a distal end of the catheter.

It is yet another object of the present invention to provide a catheter, as above, in which the thread is secured at one of its ends to the hub and whereupon the thread extends the length of the hollow tubular member and then exits and enters a series of holes at the distal end of the tubular member and then returns and exits out the hub to provide a thread pulling end.

It is yet another object of the present invention to provide a catheter, as above, in which the distal end of the tubular member has a loop coil portion with a series of holes extending therethrough. These series of holes include: a loop hole at the furthest end of the tube and extending through the single wall of the tubular member; a transition hole extending through opposite walls of the tubular member, somewhat closer to the hub end; and an end hole extending through just one wall of the tubular member, even closer to the hub member. The thread, after extending the length of the tubular member, exits the loop hole and then enters and exits through the transition hole and re-enters the tubular member at the end hole.

It is still another object of the present invention to provide a catheter, as above, in which a pulling force applied to the thread causes the distal end to form a first loop and then a second loop once the thread is pulled through the transition hole and the end hole.

It is still a further object of the present invention to provide a catheter, as above, wherein the loop hole, the transition holes, and the end hole are aligned with one another when the loops are fully formed. The hub provides a pivotable locking device to hold the thread in place so that the loops stay formed through its intended use. It is a further object of the present invention to allow for releasing of the pivotable locking member so that the loops relax and allow extraction of the catheter.

The foregoing and other objects of the present invention, which shall become apparent as the detailed description proceeds, are achieved by a catheter, comprising an elongated tubular member having a proximal end opposite a distal end, the distal end having a loop hole, at least one transition hole, and an end hole, and a thread having one end fixed at the proximal end, the thread extending through the tubular member and out from theloop hole, the thread extending through the transition hole and re-entering the tubular member at the end hole, the thread having a pulling end exiting the tubular member at the proximal end, wherein application of a pulling force on the pulling end causes the distal end to form a first loop from the loop hole to the transition hole and a second loop from the transition hole to the end hole.

It is an additional object of the present invention to a multi-loop catheter comprising a hollow tubular member having a proximal end opposite a distal end, the hollow tubular member preformed into a multiple-loop configuration, such that after insertion into a cavity, the tubular member substantially returns to its preformed shape.

These and other objects of the present invention, as well as the advantages thereof over existing prior art forms, which will become apparent from the description to follow, are accomplished by the improvements hereinafter described and claimed. In general, a catheter made in accordance with the present invention includes an elongated tubular member having a proximal end opposite a distal end. The distal end has a loop hole, at least one transition hole, and an end hole extending transversely therethrough. A thread having one end fixed at the proximal end extends through the tubular member and out from the loop hole and then enters into the transition hole and therethrough and then re-enters the tubular member at the end hole. The thread has a pulling end exiting the tubular member at the proximal end. A hub, which has a channel therethrough, is coupled to the proximal end of the tubular member. Application of a pulling force on the pulling end causes the distal end of the catheter to form a first loop from the loop hole to the transition hole and then a second loop from the transition hole to the end hole. These loops stay formed when the thread is held in place.

In accordance with other aspects of the present invention, the catheter provides drainage/infusion ports between the distal end and the end hole. Additionally, the hub has a pivotable locking member coupled thereto, wherein the locking member secures the pulling end of the thread to the hub after the thread is fully pulled.

A preferred catheter, incorporating the concepts of the present invention, is shown by way of example in the accompanying drawings without attempting to show all the various forms and modifications in which the invention might be embodied, the invention being measured by the appended claims and not by the details of the specification.

BRIEF DESCRIPTION OF THE DRAWINGS

For a complete understanding of the objects, techniques and structure of the invention, reference should be made to the following detailed description and accompanying drawings, wherein:

FIG. 2 is an elevational view, in partial cross-section, showing the multi-loop catheter partially formed;

FIG. 3 is an end view of the multi-loop catheter taken substantially along line 3—3 of FIG. 2;

PREFERRED EMBODIMENT FOR CARRYING OUT THE INVENTION

Figure 1:
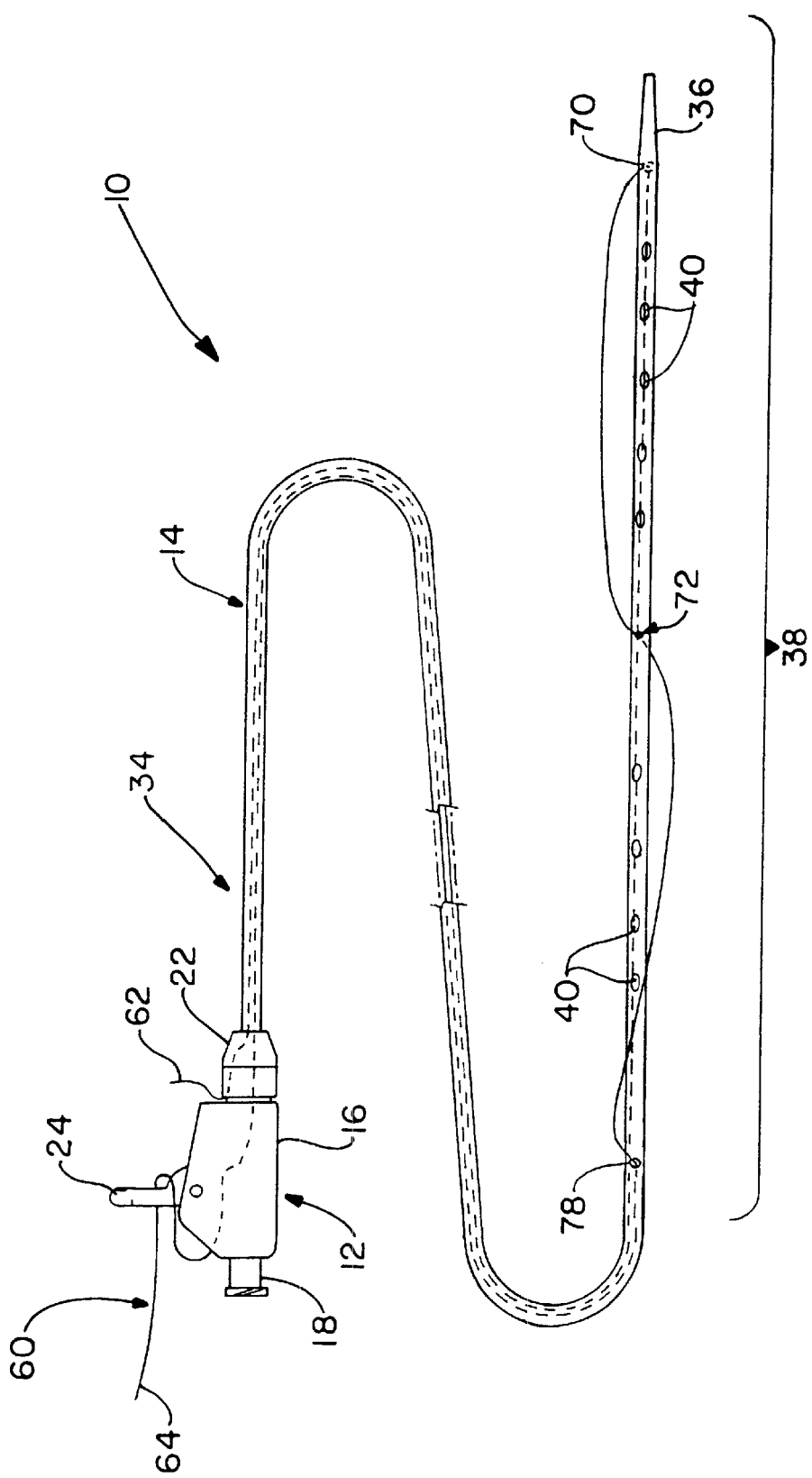
FIG. 1 is an elevational view, partially broken-away, of a multi-loop catheter according to the present invention.

A multi-loop catheter for use with draining excess or infected fluid from a body cavity or for infusing medication into the body cavity, made in accordance with the concepts of the present invention, is indicated generally by the numeral 10 in the accompanying drawings, and is best seen generally in FIGS. 1 and 2. The primary components of the catheter 10 include a hub, generally indicated by the numeral 12, and an elongated hollow tubular member, generally indicated by the numeral 14. The hub 12 is typically made of a plastic semi-rigid material, while the tubular member is made of a flexible polymeric material, such as Ultrathane™. Those skilled in the art will appreciate that the materials selected for the hub and the tubular member comply with the necessary regulations for medical devices.

The hub 12 includes a body 16 that has a coupling end 18, through which extends a channel 20. The coupling end 18 is usually connected or installed to another device upon insertion of the catheter 10 into a body cavity. The other device may be a vessel for collecting the excess or infected fluid or the like, or a medication delivery system. The channel 20 is aligned with and connected to the tubular member 14 by a collar 22. The collar 22 is typically threaded unto the body 16, but other means for attachment may be employed.

A pivotable locking member 24 is mounted on the hub 12. The locking member 24 is supported by a frame 26 extending from the body 16. The body 16 has a collar hole 28, which transversely extends through the body 16 and into the channel 20. The frame 26 provides a frame hole 30 which is in relatively close proximity to the collar hole 28.

The tube 14 includes a proximal end 34 adjacent the hub 12 and a distal end 36 opposite the proximal end 34. In the preferred embodiment, the distal end 36 is pointed or tapered to facilitate insertion into the body cavity. The distal end 36 includes a multiple loop-forming portion, designated generally by the numeral 38. The multiple loop-forming portion 38 extends from the distal end 36 toward the proximal end 34 and, in the preferred embodiment, is anywhere 1 to 4 inches in length. Of course, other lengths could be employed. Moreover, the loop-forming portion 38 is preferably preformed such that, in its relaxed position, with the stiffening cannula removed, a multiple loop configuration is naturally formed. FIG. 1 shows the distal end in a rod-like configuration to clearly show the structural features thereof. Pre-forming of the catheter facilitates its coiling as described in detail below.

The multiple loop-forming portion 38 includes at least one drainage/infusion port 40 and typically includes a port 40 about every ½ inch of the tubular member 14. When the catheter is inserted into the body cavity, excess fluid migrates into the ports 40, whereupon it travels the length of the tubular member and exits through the channel 20. The excess fluid may flow by force of gravity or may be extracted using a syringe. Those skilled in the art will appreciate that the ports 40 could also be employed to infuse medication to assist in treating the patient or to break up material contained within the cavity so that it may be later withdrawn by the catheter.

The hollow tubular member 14 includes a wall 44 which provides an exterior 46 opposite an interior 48. It will be appreciated that the ports 40 are preferably radially aligned on one side and equally spaced along the length of the portion 38. Although the ports 40 could be arbitrarily positioned anywhere along the portion 38, it is preferred that they have a single radial alignment so as to ensure that they are never blocked by the tubular member after it is coiled or by the cavity into which the catheter is inserted.

In order to transform the portion 38 from a relaxed configuration, the thread 60 extends through the tubular member from the proximal end to the distal end and back. Those skilled in the art will appreciate that the portion 38 may be pre-formed so as to impart a double- or multiple-loop shape to the portion so as to facilitate its coiling. In any event, the thread 60 has a fixed end 62 which is captured between the body 16 and the collar 22. The thread 60 extends from the fixed end into the tubular member 14 and extends along the interior thereof all the way to the distal end 36. The thread 60 then turns from the distal end through a series of holes, in a manner to be described below, and returns through the tubular member 14 and into the channel 20 of the body 16. From there, the thread 60 has a pulling end 64 that extends into the collar hole 28 and out of the hub 12 through the frame hole 30. The thread 60 is then looped around the pivotable locking member 24. When the pivotable locking member 24 is in its upward or open position, the pulling end 64 may have a pulling force or axial force applied thereto.

The forming portion 38 includes a loop hole 70 which is located at the distal end 38 at appoint furthest from the hub 12. The loop hole 70 extends transversely through a single wall of the tubular member 14. The loop hole 70 is radially positioned substantially 180° away from the port holes 40. In other words, the loop hole 70 is substantially opposite the radial position of the port holes 40. It will also be appreciated that the size of the loop hole 70 is substantially smaller than the port holes and is sized to accommodate the diameter of the thread so that it can easily slide within the hole. The forming portion 38 also includes a transition hole 72 positioned somewhat closer to the hub 12 than the loop hole 70. The transition hole 72 includes a transition entry hole 74 and a transition exit hole 76, which are preferably aligned with one another. The entry hole 74 is realigned with the port holes 40 and extends through one side of the tubular member. The transition exit hole 76 is substantially aligned with the entry hole 74 and extends through the opposite wall of the tubular member. Accordingly, the thread 60 enters through the transition entry hole 74 and exits through the transition exit hole 76. From the exit hole 76, the thread extends outside of the tubular member 14 which has an end hole 76 which is closer to the hub than the transition hole 72. The thread 60 re-enters the tubular member at the end hole 78. The end hole 78 extends through one wall of the tubular member and is aligned in substantially the same radial position as the ports 40. Alternatively, the thread 60 could be fixed at the loop hole 70 and extend through the transition hole and the end hole as described above.

Figure 5:
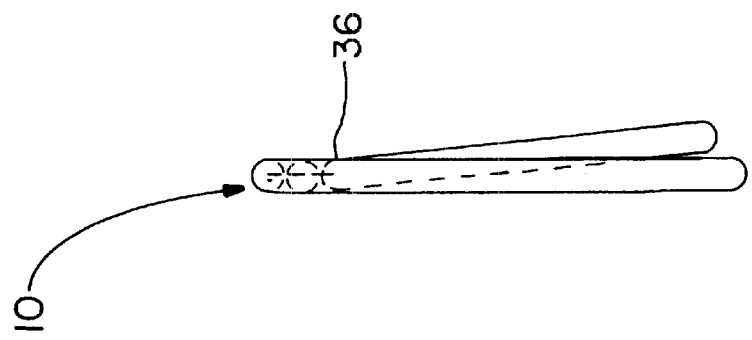
FIG. 5 is an end view of the multi-loop catheter completely coiled.
Figure 4:
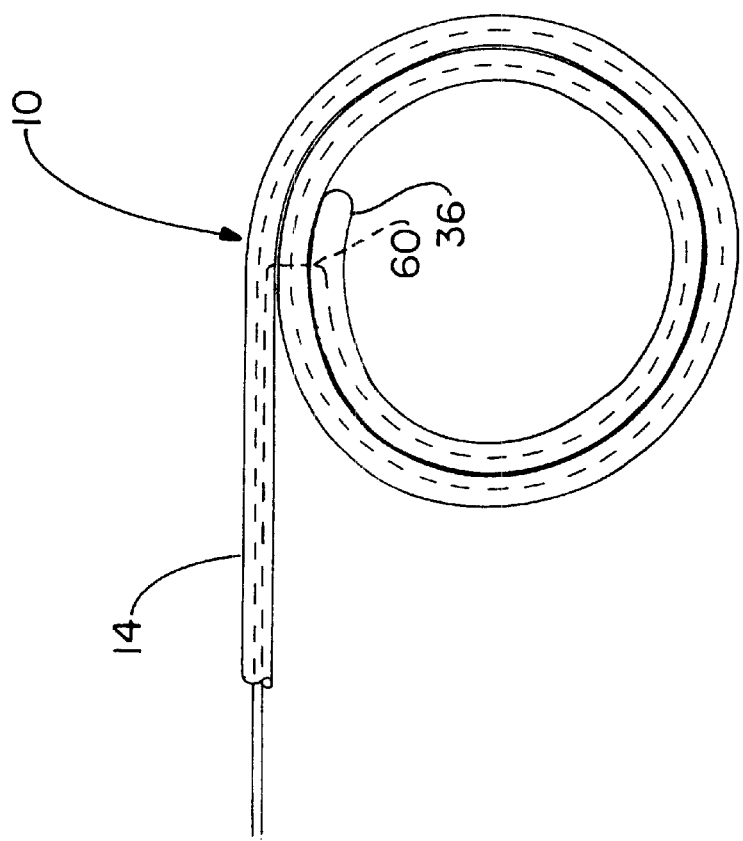
FIG. 4 is an elevational view, in partial cross-section, showing the multi-loop catheter completely coiled.

As best seen in FIGS. 2 and 3, pulling of the thread 60 begins substantial alignment of the loop hole 70 with the transition hole 72. As the pulling force is further applied, the transition hole 72 becomes substantially aligned with the end hole 78, as best seen in FIGS. 4 and 5. When the coils are fully formed, the user of the catheter 10 will pivot the locking member 24 downwardly so as to capture the pulling end and preclude uncoiling of the loops within the body cavity if the hub end were to be pulled or tugged on by the patient. The hub end could be pulled not just by the patient, but also accidentally by a nurse during dressing changes, or it might get caught on the bed rail or a closet door. As best seen in FIGS. 3 and 5, use of a double-loop provides an additional diameter or mass to preclude inadvertent withdrawal of the catheter from the body cavity. Although only one transition hole 72 is shown, it will be appreciated that multiple transition holes could be provided. These would be placed within the portion 38 and allow for formation of additional loops at the distal end of the tubular member.

From the foregoing description, the advantages of the present invention are readily apparent. First, instead of forming a single loop, a double loop or multiple loops can be formed by employing an additional transition hole extending transversely through the tubular member 14. This further secures the distal end 38 of the catheter within the body cavity and precludes its inadvertent withdrawal therefrom. This is attributed to the additional thickness of the added coils and also because of the additional length of the tubular member coiled within the body cavity. By forming more than one loop, the catheter provides greater diameter and mass which improves retention. Yet another advantage of the present invention is that the multiple loops can be formed without any additional training for the person inserting the catheter as its operation is similar to that of a single-loop catheter. It will also be appreciated that the radial and axial positioning of the transition, end and loop holes can be changed such that when the thread is pulled, shapes other than round coils can be formed. For example, the loops may extend in opposed angular directions with different orientations. Use of different angular orientations may be necessitated by the cavity into which it is to be placed. Although a thread is the preferred mechanism for forming the coils, use of other slidable members could be used, such as a ribbon or the like.

Thus, it can be seen that the objects of the invention have been satisfied by the structure and its method for use presented above. While in accordance with the Patent Statutes, only the best mode and preferred embodiment has been presented and described in detail, it is to be understood that the invention is not limited thereto or thereby. Accordingly, for an appreciation of true scope and breadth of the invention, reference should be made to the following claims.

What is claimed is:

1. A catheter, comprising:
   an elongated tubular member having a proximal end opposite a distal end, said distal end having a loop hole, at least one transition hole, and an end hole; and
   a thread having one end fixed at said proximal end, said thread extending through said tubular member and out from said loop hole, said thread extending through said transition hole and re-entering said tubular member at said end hole, said thread having a pulling end exiting said tubular member at said proximal end, wherein application of a pulling force on said pulling end causes said distal end to form a first loop from said loop hole to said transition hole and a second loop from said transition hole to said end hole.

2. The catheter according to claim 1, wherein said tubular member has at least one drainage/infusion port between said distal end and said end hole.

3. The catheter according to claim 1, wherein said tubular member has a plurality of drainage/infusion ports between said distal end and said end hole, said ports in a radial position substantially opposite the radial position of said loop hole.

4. The catheter according to claim 1, wherein said tubular member has a wall through which said loop hole extends.

5. The catheter according to claim 4, wherein said transition hole extends through said wall in two places, said transition hole including an entry hole extending through said wall in one place and an exit hole extending through said wall at a radial position substantially opposite said entry hole.

6. The catheter according to claim 5, wherein said end hole is in the same radial orientation as said entry hole.

7. The catheter according to claim 6, wherein said loop hole, said entry and exit holes, and said end hole are substantially axially aligned with one another when said thread is fully pulled.

8. The catheter according to claim 1, further comprising:
   a hub having a channel therethrough, said hub coupled to said tubular member; and
   a pivotable locking member coupled to said hub, said locking member securing said thread to said hub after said thread is fully pulled.

9. A multi-loop catheter comprising:
   a hollow tubular member having a proximal end opposite a distal end, said hollow tubular member preformed into a multiple-loop configuration, such that after insertion into a cavity, said tubular member substantially returns to its preformed shape,
   a thread extending from at least said proximal end to said distal end, wherein pulling of said thread assists in returning said tubular member to its preformed shape after insertion into the cavity,
   said distal end having a loop hole; a transition hole, closer to said proximal end than said loop hole, said transition hole extending through both walls of said tubular member; and an end hole closer to said proximal end than said transition hole, wherein said thread extends from said loop hole through said transition hole and into said end hole which returns to said proximal end, whereby when said thread is pulled, the preformed multiple loops are reformed and held in place.

10. The multi-loop catheter according to claim 9, wherein said thread is secured at one end to said proximal end, said thread extending from said proximal end to said distal end, extending through said loop, transition, and end holes and returning to said proximal end where said thread is grasped and pulled.

11. The multi-loop catheter according to claim 9 wherein said tubular member has a plurality of drainage/infusion ports between said end hole and said loop hole.

12. The catheter according to claim 11, further comprising:

a hub having a channel therethrough, said hub coupled to said tubular member; and a pivotable locking member coupled to said hub, said locking member securing said thread to said hub after said thread is fully pulled.

13. A catheter comprising:

an elongated tubular member having a proximal end opposite a distal end, said distal end having a loop hole, at least one transition hole, and an end hole, wherein said tubular member has a wall through which said loop hole extends, wherein said transition hole extends through said wall in two places, said transition hole including an entry hole extending through said wall in one place and an exit hole extending through said wall at a radial position substantially opposite said entry hole; and a thread having one end fixed at said proximal end, said thread extending through said transition hole and re-entering said tubular member at said end hole, said thread having a pulling end exiting said tubular member at said proximal end, wherein application of a pulling force on said pulling end causes said distal end to form a first loop from said loop hole to said transition hole and a second loop from said transition hole to said end hole.

14. The catheter according to claim 13, wherein said end hole is in the same radial orientation as said entry hole.

15. The catheter according to claim 14, wherein said loop hole, said entry and exit holes, and said end hole are substantially axially aligned with one another when said thread is fully pulled.

* * * * *